(12) United States Patent
Triebes et al.

(10) Patent No.: US 7,534,224 B2
(45) Date of Patent: May 19, 2009

(54) CATHETER WITH UNITARY COMPONENT

(75) Inventors: Thomas Gregory Triebes, Alpharetta, GA (US); Michael Allen Kenowski, Pocatello, ID (US); Donald J. McMichael, South Jordan, UT (US); Netty Dawn DiViesti, Pocatello, ID (US); Daniel Kermit Hill, Blackfoot, ID (US)

(73) Assignee: Kimberly-Clark Worldwide, Inc., Neehah, WI (US)

( * ) Notice: Subject to any disclaimer, the term of this patent is extended or adjusted under 35 U.S.C. 154(b) by 0 days.

(21) Appl. No.: 10/306,999

(22) Filed: Nov. 30, 2002

(65) Prior Publication Data

US 2004/0106900 A1 Jun. 3, 2004

(51) Int. Cl.
*A61M 29/00* (2006.01)
(52) U.S. Cl. ...................................... 604/104
(58) Field of Classification Search .............. 604/96.01, 604/103.06, 104, 915, 93.01, 103, 103.09, 604/174, 175, 264, 910, 103.08
See application file for complete search history.

(56) References Cited

U.S. PATENT DOCUMENTS

| | | | |
|---|---|---|---|
| 1,598,283 A | 8/1926 | Kinney | |
| 3,050,066 A | * 8/1962 | Koehn | 604/97.01 |
| 3,544,668 A | 12/1970 | Dereniuk | |
| 3,865,666 A | 2/1975 | Shoney | |
| 3,915,171 A | 10/1975 | Shermeta | |
| 3,959,429 A | 5/1976 | Benning | |
| 4,157,094 A | 6/1979 | Patel | |
| 4,210,478 A | 7/1980 | Shoney | |
| 4,213,461 A | 7/1980 | Pevsner | |
| 4,227,293 A | 10/1980 | Taylor | |
| 4,284,459 A | 8/1981 | Patel et al. | |
| 4,315,513 A | 2/1982 | Nawash et al. | |
| 4,393,873 A | 7/1983 | Nawash et al. | |
| 4,447,228 A | 5/1984 | Patel | |
| 4,531,943 A | 7/1985 | Van Tassel et al. | |
| 4,634,435 A | 1/1987 | Ingraham | |
| 4,639,252 A | 1/1987 | Kelly et al. | |
| 4,661,095 A | 4/1987 | Taller et al. | |
| 4,666,433 A | 5/1987 | Parks | |
| 4,685,901 A | 8/1987 | Parks | |

(Continued)

FOREIGN PATENT DOCUMENTS

CA 2019886 1/1991

(Continued)

OTHER PUBLICATIONS

Patent Abstracts of Japan, Publication No. 2000254221, Sep. 19, 2000.

(Continued)

*Primary Examiner*—Kevin C Sirmons
*Assistant Examiner*—Elizabeth R MacNeill
(74) *Attorney, Agent, or Firm*—Sue C. Watson; William W. Letson; Scott B. Garrison

(57) ABSTRACT

A unitary component having a tip portion integrally formed with an expandable sleeve portion. Other aspects of the present invention are related to a catheter incorporating a unitary component. Still other aspects of the present invention will be apparent upon reading the remainder of the disclosure.

4 Claims, 7 Drawing Sheets

U.S. PATENT DOCUMENTS

| | | | |
|---|---|---|---|
| 4,737,219 A | 4/1988 | Taller et al. | |
| 4,798,592 A | 1/1989 | Parks | |
| 4,850,953 A | 7/1989 | Haber et al. | |
| 4,874,373 A | 10/1989 | Luther et al. | |
| 4,886,059 A | 12/1989 | Weber | |
| 4,927,412 A * | 5/1990 | Menasche | 604/103.08 |
| 4,950,239 A | 8/1990 | Gahara et al. | |
| 4,976,710 A | 12/1990 | Mackin | |
| 5,009,639 A | 4/1991 | Keymling | |
| 5,042,976 A | 8/1991 | Ishitsu et al. | |
| 5,074,845 A | 12/1991 | Miraki et al. | |
| 5,076,268 A | 12/1991 | Weber | |
| 5,080,650 A | 1/1992 | Hirsch et al. | |
| 5,087,394 A | 2/1992 | Keith | |
| 5,125,897 A | 6/1992 | Quinn et al. | |
| 5,137,671 A | 8/1992 | Conway et al. | |
| 5,156,612 A | 10/1992 | Pinchuk et al. | |
| 5,160,321 A * | 11/1992 | Sahota | 604/101.03 |
| 5,195,969 A | 3/1993 | Wang et al. | |
| 5,250,040 A | 10/1993 | Parks et al. | |
| 5,267,969 A | 12/1993 | Hirsch et al. | |
| 5,295,969 A | 3/1994 | Fischell et al. | |
| 5,308,325 A * | 5/1994 | Quinn et al. | 604/96.01 |
| 5,324,260 A * | 6/1994 | O'Neill et al. | 604/103.08 |
| 5,370,618 A | 12/1994 | Leonhardt | |
| 5,370,899 A | 12/1994 | Conway et al. | |
| 5,391,159 A | 2/1995 | Hirsch et al. | |
| 5,411,477 A | 5/1995 | Saab | |
| 5,423,760 A * | 6/1995 | Yoon | 604/164.11 |
| 5,439,444 A | 8/1995 | Andersen et al. | |
| 5,458,583 A | 10/1995 | McNeely et al. | |
| 5,514,153 A | 5/1996 | Bonutti | |
| 5,522,961 A | 6/1996 | Leonhardt | |
| 5,527,280 A | 6/1996 | Goelz | |
| 5,593,718 A | 1/1997 | Conway et al. | |
| 5,707,357 A | 1/1998 | Mikhail et al. | |
| 5,709,691 A * | 1/1998 | Morejon | 606/106 |
| 5,718,712 A | 2/1998 | Bonnal et al. | |
| 5,718,861 A | 2/1998 | Andrews et al. | |
| 5,762,996 A | 6/1998 | Lucas et al. | |
| 5,792,118 A | 8/1998 | Kurth et al. | |
| 5,807,520 A | 9/1998 | Wang et al. | |
| 5,836,924 A * | 11/1998 | Kelliher et al. | 604/248 |
| 5,860,952 A | 1/1999 | Quinn | |
| 5,860,960 A | 1/1999 | Quinn | |
| 5,865,721 A | 2/1999 | Andrews et al. | |
| 5,865,816 A | 2/1999 | Quinn | |
| 5,879,499 A * | 3/1999 | Corvi | 604/524 |
| 5,891,113 A | 4/1999 | Quinn | |
| 5,910,128 A | 6/1999 | Quinn | |
| 5,938,585 A | 8/1999 | Donofrio | |
| 5,971,954 A | 10/1999 | Conway et al. | |
| 5,997,503 A | 12/1999 | Willis et al. | |
| 5,997,546 A * | 12/1999 | Foster et al. | 606/108 |
| 6,013,054 A | 1/2000 | Jiun Yan | |
| 6,077,243 A | 6/2000 | Quinn | |
| 6,129,713 A * | 10/2000 | Mangosong et al. | 604/264 |
| 6,136,258 A | 10/2000 | Wang et al. | |
| 6,168,748 B1 | 1/2001 | Wang et al. | |
| 6,248,121 B1 | 6/2001 | Nobles | |
| 6,264,631 B1 * | 7/2001 | Willis et al. | 604/96.01 |
| 6,287,277 B1 | 9/2001 | Yan | |
| 6,328,720 B1 | 12/2001 | McNally et al. | |
| 6,447,472 B1 | 9/2002 | Moss | |
| 6,506,179 B1 * | 1/2003 | Tiefenthal et al. | 604/103.06 |
| 6,524,283 B1 * | 2/2003 | Hopper et al. | 604/264 |
| 6,740,273 B2 | 5/2004 | Lee | |
| 2001/0035590 A1 | 11/2001 | Nishi et al. | |
| 2002/0091365 A1 | 7/2002 | McNally et al. | |
| 2002/0198440 A1 | 12/2002 | Snow | |
| 2002/0198491 A1 | 12/2002 | Miller et al. | |
| 2003/0225369 A1 | 12/2003 | McMichael et al. | |

FOREIGN PATENT DOCUMENTS

| | | |
|---|---|---|
| CA | 1299954 | 5/1992 |
| CA | 2347208 | 4/2000 |
| DE | 9208103 U | 3/1993 |
| EP | 0347458 B1 | 3/1994 |
| EP | 0409436 B1 | 12/1994 |
| EP | 0943354 A1 | 9/1999 |
| GB | 2 218 372 A | 11/1989 |
| WO | WO 88/05316 | 7/1988 |
| WO | WO 00/23136 | 4/2000 |
| WO | WO 00/40289 | 7/2000 |
| WO | WO 02/22198 A2 | 3/2002 |
| WO | WO 02/051490 | 7/2002 |
| WO | WO 02/087492 | 11/2002 |
| WO | WO 03/032892 A2 | 4/2003 |

OTHER PUBLICATIONS

Patent Abstracts of Japan, Publication No. 03277374 A, Dec. 9, 1991.
"PEG Percutaneous Endoscopic Gastrostomy", Brochure, one page, Create Medic Co., Ltd, 2002.
"Replacement Catheter", Japanese Brochure, one page, 2003.

* cited by examiner

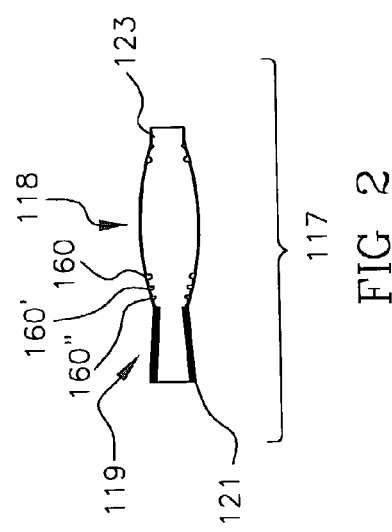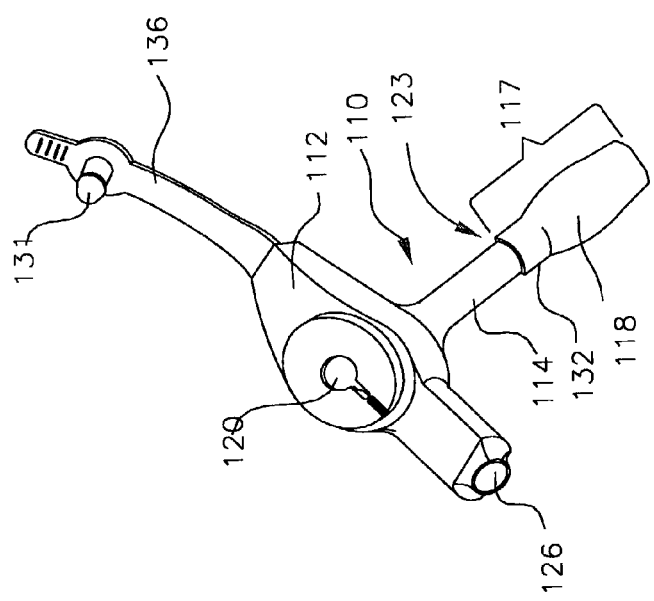

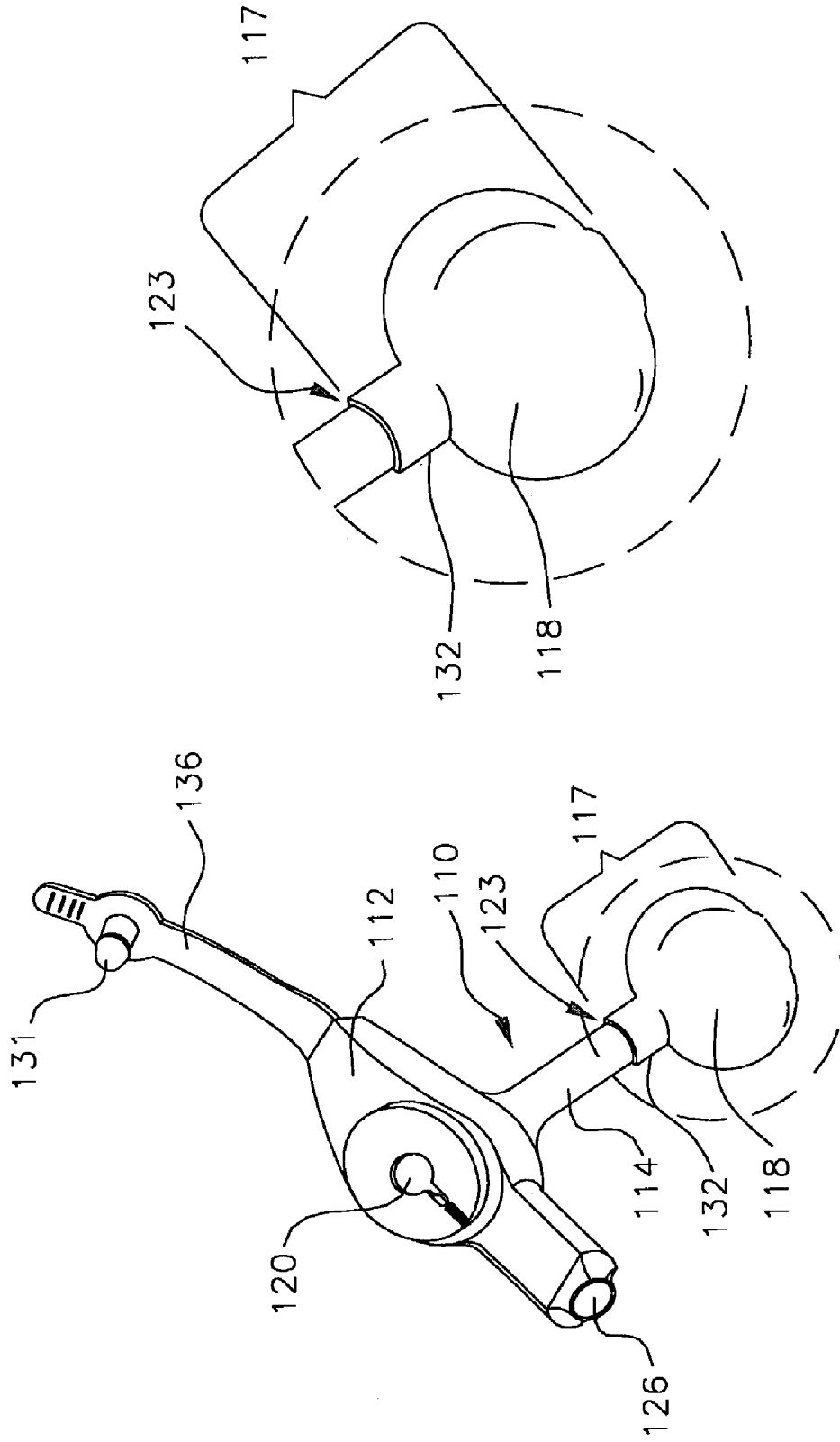

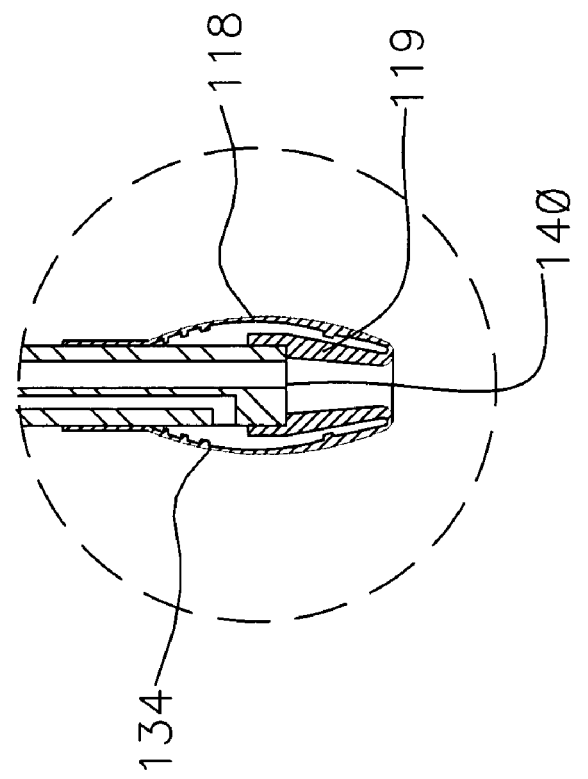
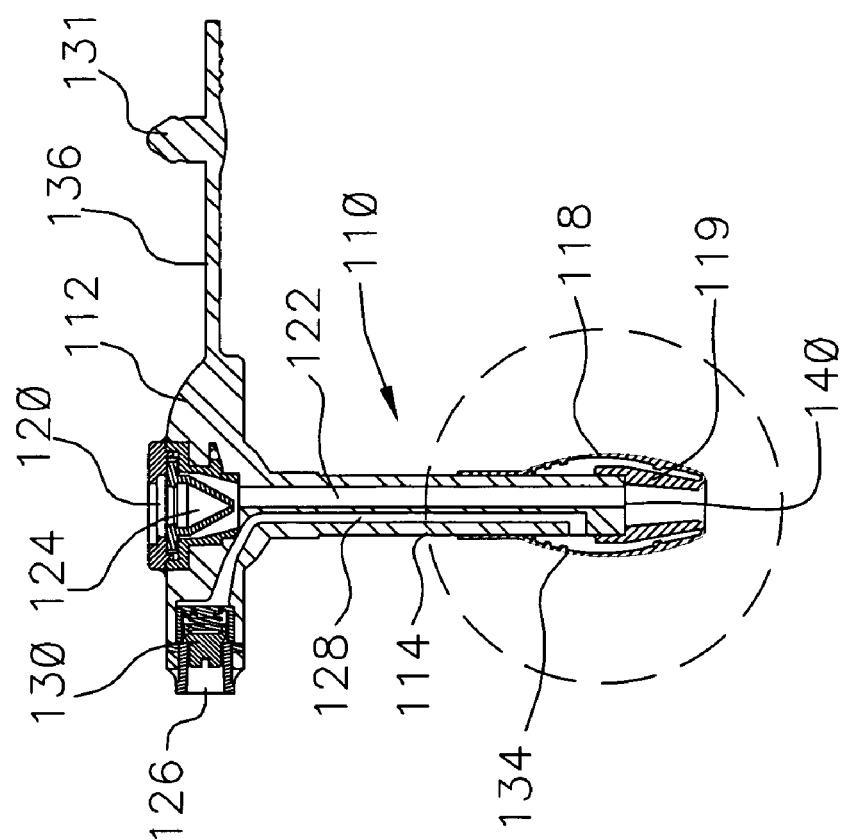
FIG 5A
FIG 5

CATHETER WITH UNITARY COMPONENT

BACKGROUND

Catheterization of a body cavity is frequently performed in medical procedures either to insert substances into or to remove substances from the body. During many of these procedures, it is necessary to keep the catheter in a relatively stable position to perform the desired insertion or removal. With the use of enteral feeding catheters (i.e., catheters which enable the administration of nutritional solutions directly into the stomach or intestines), for example, it is necessary to ensure that the catheter is not accidentally removed from the stomach or intestines. This is true both during the actual administration or removal of fluids, and the time periods in between.

In order to ensure that a catheter is maintained in the proper position, it is common to use a balloon disposed near the distal (patient) end of the catheter shaft. Inflating the balloon causes the balloon to contact the anatomical structure (i.e., a duct or stomach wall) and thereby prevents the catheter from moving out of the proper position. In the case of enteral feeding, a stoma is formed leading into the stomach or intestine. The catheter is positioned to extend through the stoma so as to form a channel into the stomach or intestines through which enteral feeding solutions may be instilled.

FIG. 1 shows a side view of a prior art balloon catheter 10 having a head 14 disposed at a proximal end 15. The head 14 contains valves (not shown) which regulate the flow of fluids through the balloon catheter 10. The head 14 also prevents the balloon catheter 10 from completely advancing through the stoma and into the stomach or intestine of the user.

To prevent the catheter 10 from being pulled out of the stomach/intestinal wall, a balloon 18 is disposed along a catheter shaft 26. The catheter 10 is shown having an optional stiff tip 30, which is attached to the catheter shaft 26 at a distal end 17 opposite the head 14. The catheter shaft 26 is typically made of a medical grade silicone. The stiff tip 30, when present, is also frequently formed of a medical grade silicone but is usually configured to be as rigid as or less rigid than the catheter shaft 26.

The balloon 18 is advantageous because it allows the catheter shaft 26 to be inserted into the stoma (not shown) while the balloon 18 is uninflated. Once the catheter shaft 26 is properly positioned in the stoma, a syringe (not shown) is inserted into a side port 36 of the head 14 and a fluid is injected into the balloon 18 through a lumen (not shown in FIG. 1) of the catheter 10 so as to inflate the balloon 18.

While the balloon 18 remains inflated, the catheter 10 stays properly positioned in the stoma. The position of the balloon catheter 10 is maintained in such a manner until removal is desired. If the catheter 10 needs to be removed, the balloon 18 may be deflated so that it will not interfere with withdrawal of the catheter shaft 26 and stiff tip 30.

The type of balloon 18 shown in FIG. 1 is fashioned around the perimeter of the catheter shaft 26 such that when it is deflated it reduces or contracts about the shaft 26 but is still clearly larger than overall diameter of the catheter.

Attachment of the balloon 18 to the catheter shaft 26 is frequently accomplished by gluing the balloon proximal end 20 and the balloon distal end 22 to corresponding positions on the external surface of the catheter shaft 26 so as to form a proximal cuff 32 and a distal cuff 34, respectively. Such cuffs 32 and 34 are longitudinal sections of the balloon 18 whose inside diameters correspond to the outside diameter of the shaft 26 at their respective points of attachment to the catheter 10 and have a distance between them which is about the length of the uninflated balloon 18. The cuffs 32 and 34 must be of sufficient length to provide a tight and durable seal between the balloon 18 and the catheter shaft 26.

While the prior art balloon configuration shown in FIG. 1 works to maintain the balloon catheter 10 in the proper position within the patient, balloon catheters of this type as well as the other known balloon catheters do have disadvantages. For example, one drawback of prior balloon catheters is discomfort to the user. With regard to the catheter of FIG. 1, in order to allow insertion of the catheter 10, the catheter shaft 26 and especially the stiff tip 30 must be relatively rigid or firm to prevent buckling under insertion pressures. However, this same firmness makes the distal tip 30 much more prone to irritate anatomical structures which come into contact with it. This is especially true in the stomach and intestines where the opposing walls of the anatomical structures tend to collapse on each other during physical exertion or when the cavity has little or no food. As the person moves, the stiff tip 30 repeatedly engages the adjacent anatomical structure (such as the stomach wall) and can lead to irritation and/or discomfort for the user. Thus, as the presence of an extended stiff catheter tip in this environment has been suspected of irritating the opposing surfaces of the body cavity, it would be desirable if the patient could be protected from exposure to the tip 30.

Accordingly, there is a need in the art for a balloon catheter with a stiff distal tip isolated from opposing internal body cavity surfaces.

Another disadvantage with the prior art balloons of the type discussed above, is that if they were to be secured to the interior portion of the tip 30 they would provide undesirable restriction of the flow of fluids therethrough. Although not done in prior catheters, if the tip were to be attached to the interior of the catheter shaft, the flow would be further reduced. The reduction in flow can result in the need for longer use of the catheter to obtain the desired level of fluid flow. If a catheter having a wider tip or shaft is used to overcome the fluid flow issue, the stoma through which the catheter must be inserted will need to be larger thereby creating other issues, such as increased time for the stoma to heal as well as creating a larger opening through which fluids can leak out.

Accordingly, there is a need for a catheter which can provide for an increased level of fluid flow (as compared with prior devices) without the need for a larger stoma opening.

Yet another disadvantage with prior art catheters of the type discussed above is that they generally first require the separate manufacture of multiple pieces (e.g., the catheter, the rigid tip and the balloon), then the attachment of the tip to the catheter and one end of the balloon and, finally, the attachment of the second end of the balloon to the catheter. Each of the attachments methods have been done manually in the past. Naturally, this manual operation is slow, costly and inefficient. Further with each additional step in a process there exists an opportunity for error and waste of product.

Thus, while there is a need for catheters, because of the number of individual pieces or members which comprise a catheter and because those pieces are typically assembled by hand or at least in multiple assembly steps, there is a need in the art for a catheter which requires less assembly, and specifically less manual assembly.

SUMMARY OF THE INVENTION

In response to the difficulties and problems discussed above, a unitary component which may be used with catheters has been developed. More specifically, one embodiment of the invention relates to a unitary component having a tip integrally formed with an expandable sleeve portion.

Another embodiment of the present invention relates to a catheter having a unitary tip. More specifically, the catheter includes an elongate shaft and a unitary component. More specifically still, the elongate catheter has a distal end, a first lumen adapted for fluid communication, an exterior, and a second lumen adapted for fluid communication with a cavity defined by the exterior of the shaft and the unitary component. The unitary component includes a tip region integrally formed with an expandable region.

Yet another embodiment of the present invention is directed to a balloon catheter having a head with at least two openings; a catheter segment extending from the head, the catheter segment having a first and second lumen disposed in communication with the at least two openings; and a balloon formed by a sleeve at a first end of a unitary component, the first end attached to the exterior of the catheter segment so as to form a first cuff and a second end of the unitary component having a tip portion and being attached to the distal end of the catheter segment.

These and other features and advantages will be seen from the following detailed description of the drawings and from the claims.

BRIEF DESCRIPTION OF THE DRAWINGS

The above and other objects, features and advantages of the invention will become apparent from a consideration of the subsequent detailed description presented in connection with the accompanying drawings in which:

FIG. 2 is a cross-sectional view of an embodiment of a unitary component made in accordance with the present invention having a tip portion and a balloon or elongate sleeve portion;

FIG. 3 is a perspective view of an embodiment of a balloon catheter of the present invention having an uninflated balloon;

FIG. 4 is a perspective view of the balloon catheter of FIG. 3 with the balloon inflated;

FIG. 4A is an enlargement of the encircled area of FIG. 4;

FIG. 5 is a cross-sectional view of the balloon catheter of FIG. 3;

FIG. 5A is an enlargement of the encircled area of FIG. 5;

FIG. 6A is an enlargement of the encircled area of FIG. 6;

DETAILED DESCRIPTION OF THE PRESENT INVENTION

Figure 1:
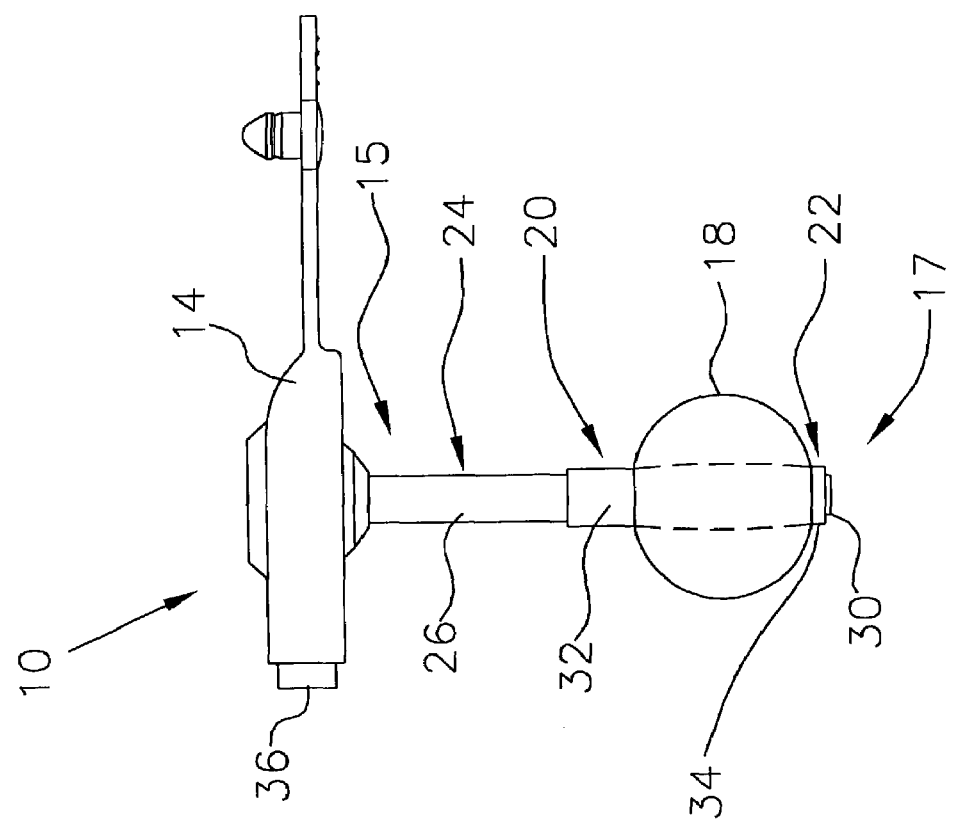
FIG. 1 is a side view of a prior art balloon catheter in an inflated configuration.

One embodiment of the present invention relates to a unitary component having a tip portion integrally formed with an expandable sleeve portion. In some embodiments the tip portion of the unitary component may be stiff or rigid.

Another embodiment of the present invention is directed to a catheter having an elongate shaft and a unitary component having a tip region integrally formed with an expandable region. The elongate shaft should have a distal end, a first lumen adapted for fluid communication, an exterior, and a second lumen adapted for fluid communication with a cavity defined by the exterior of the shaft and the unitary component. It will be appreciated that the size and shape of the cavity defined by or between the exterior of the shaft and the expandable region of the unitary catheter is variable.

As used herein, the term "distal" refers to the direction of the patient and the term "proximal" refers to the direction of the clinician.

Yet another embodiment of the present invention is directed to a balloon catheter having a head with at least two openings through which fluid may pass; a catheter shaft or segment extending from the head, the catheter shaft having a first and second lumen, each of the lumens being disposed in communication with at least one of the at least two openings; and a balloon formed by a sleeve at a first end of a unitary component, the first end of the unitary component being attached to the exterior of the catheter shaft so as to form a first cuff, and a second end of the unitary component having a tip portion and being attached to the distal end of the catheter shaft. The sleeve being such that it will generally collapse about the catheter shaft when not inflated.

It will be appreciated that while reference is made to an expandable sleeve portion in the claims and in the first part of the disclosure, the term expandable sleeve portion may also mean or include, but is not limited to, a balloon, a sleeve, an elongate sleeve, an expandable sleeve, an expandable region or portion, an inflatable member, any other suitable means for expansion or the like. However, for ease of reading and understanding of this disclosure and not intending to be limited thereby, the term expandable sleeve portion will hereinafter be referred to as a balloon. It will also be appreciated that throughout the disclosure reference is made to inflation of the balloon, however, the present invention is not intended to be limited only to inflation. That is, while inflation is used herein for purposes of ease of reading and understanding the disclosure, the term inflation is also intended to mean or include, but is not limited to, expansion, enlargement, swelling or the like.

It will be appreciated that while reference is made to a tip portion in the claims and in the first part of the disclosure, the term tip portion is contemplated to mean or include, but is not limited to, tips of all shapes and sizes, a tip member, tip, tip region, the portion of the unitary component containing the tip, and the like. However, for ease of reading and understanding of this disclosure and not intending to be limited thereby, the term tip portion will hereinafter be referred to as a tip.

Reference will now be made to the drawings in which the various elements of the present invention will be given numeral designations and in which the invention will be discussed so as to enable one skilled in the art to make and use the invention. It should be appreciated that each example is provided by way of explaining the invention, and not as a limitation of the invention. For example, features illustrated or described with respect to one embodiment may be used with another embodiment to yield still a further embodiment. These and other modifications and variations are within the scope and spirit of the invention.

Referring now to FIG. 2, there is shown a unitary component 117 having a tip 119 and a balloon 118. The tip 119 of the component 117 may be stiff or rigid, or at least as stiff as and/or more rigid than the balloon 118 and/or the catheter shaft 114 (FIG. 3), when present, as described below.

Figure 6:
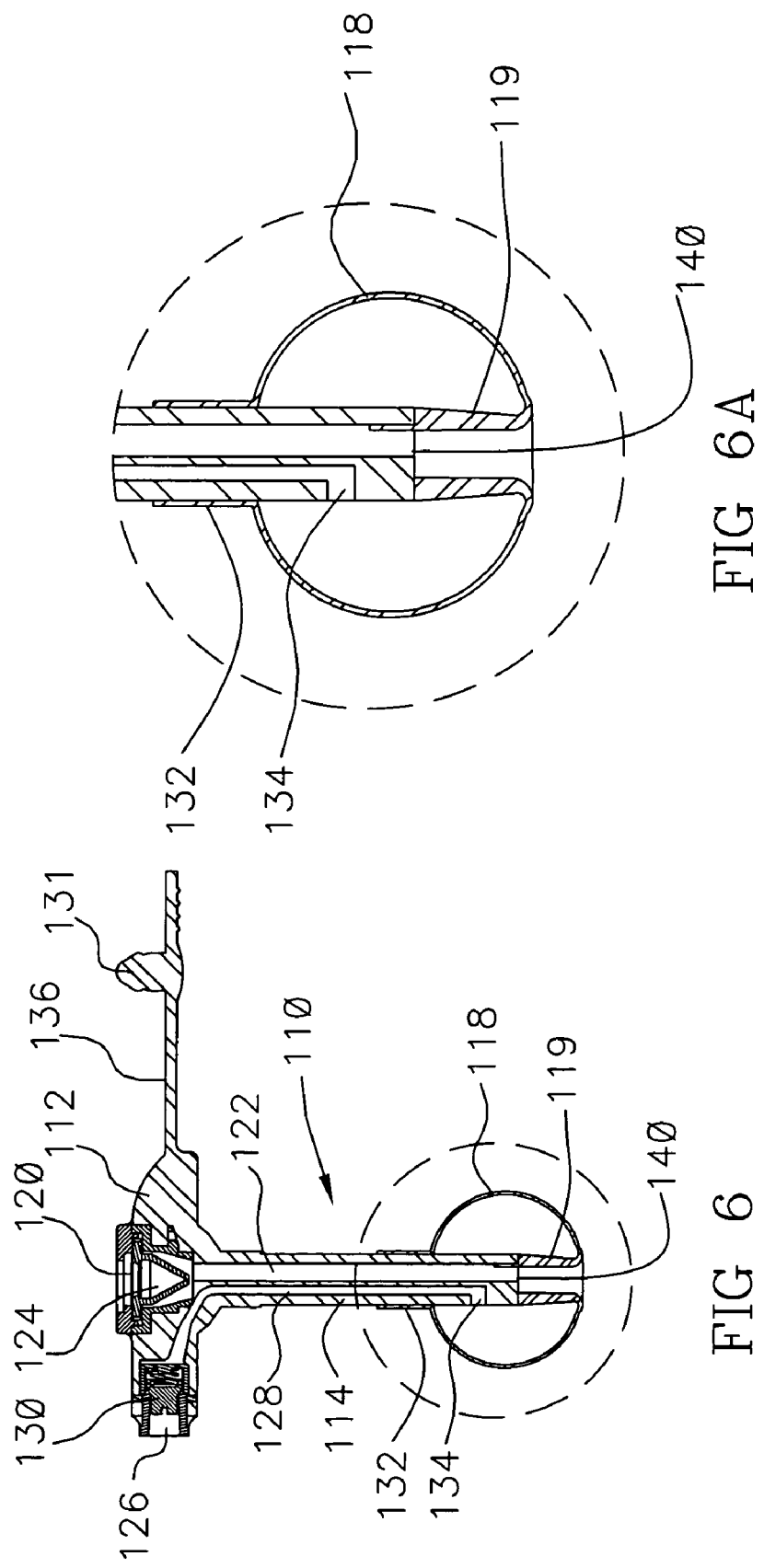
FIG. 6 is a cross-sectional view of the balloon catheter of FIG. 3, except that FIG. 6 shows an alternative attachment unitary component to the catheter.

The unitary component 117 of FIG. 2 is generally used in conjunction with a catheter such as balloon catheter 110 in FIGS. 3-8. The catheter 110 includes a proximal head 112, a shaft 114 and a unitary component 117. Referring now to FIGS. 5 and 6, the head 112 has a proximal opening 120 to a feeding lumen 122 within the shaft 114, for bolus feeding, or providing other nutrient fluids, formula, or the like to a patient (not depicted). Although not required, an anti-reflux valve 124, which is generally included to prevent back-flow of the nutrient formula, is shown disposed between the opening 120 and the feeding lumen 122. Inflation port 126 is disposed in head 112 and communicates with the inflation lumen 128 which extends longitudinally through the shaft 114. The inflation lumen 128 terminates laterally to the shaft 114 at port 134 into the cavity 135 created by the balloon 118 of the unitary component 117 and the shaft 114, as discussed in more detail below. A one-way valve 130 may be disposed between the inflation port 126 and inflation lumen 128. Application of positive fluid pressure, such as with air or saline, within and/or upon the inflation lumen 128 by way of the inflation port 126 may cause the balloon 118 of the unitary component 117 to inflate. Valve 130 helps prevent inadvertent deflation of the balloon 118. Also shown associated with the head 112 is a plug 131 for the proximal opening 120 and a lanyard 136 for retaining the plug 131 in a ready position. The plug 131 can be inserted in the opening 120 thereby reducing or precluding contamination when the opening 120 is not in use. Feeding lumen 122 extends longitudinally through shaft 114 and terminates at the distal end 140 of the shaft 114.

The various components of balloon catheter 110 may be made of any suitable material and may desirably be formed from bio-compatible materials such as medical grade silicone or the like. As above, valves 124 and 130 may be formed of any suitable material but are desirably made of a suitable polymer such as polycarbonate.

Generally, for ease of prior manufacturing concerns, the catheters and the tips of the prior devices were made separately and later assembled. Reasons for separate manufacture in the past include, but are not limited to, that it was desirable in one or more instances for the tip 30 (FIG. 1) to be made of a material different from that used to construct the catheter 10 (FIG. 1), or if made of the same material for the tip 30 to exhibit different physical properties (e.g., as a result of different processing conditions or steps) from the catheter 10. In either case (i.e. manufactured as one piece (with the catheter) or as multiple pieces), it will be appreciated that the tip 119 (FIGS. 5-8) and shaft 114 of the present invention desirably should be able to withstand insertion pressures without binding or buckling.

Figure 7:
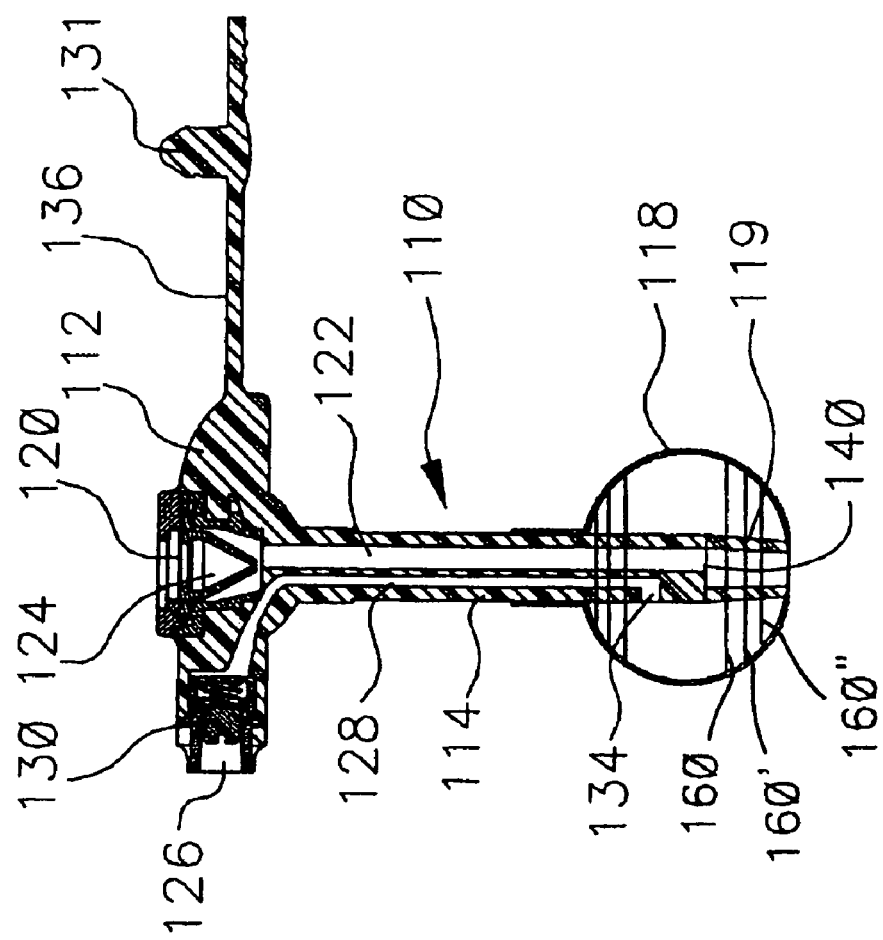
FIG. 7 is a cross-sectional view of the balloon catheter similar to that of FIG. 6, except that FIG. 7 shows an alternative attachment of the distal end of the tip of the unitary component.

The unitary component 117 of the present invention may be constructed in any number of suitable manners, including, but not limited to, injection molding, transfer molding or dipping. Further, the unitary component 117 may be attached to the catheter 110 in a variety of manners, including, but not limited to, gluing or attachment during one of the injection molding, transfer molding or dipping processes referred to above. The unitary component 117 could also be attached to the catheter 110 by way of chemical bonding, such as solvent bonding. As shown in FIGS. 5 and 5A, unitary component 117 may be attached to the catheter 110 in such a way as to overlap with the distal end 140 of the catheter 110. The overlap may be on the exterior (FIGS. 5 and 5A) of the catheter shaft 114 or the interior (FIGS. 6 and 6A) of the shaft 114. Alternately, as shown in FIG. 7, the unitary component 117 may, for example, be attached to the end 140 of the catheter shaft 114 in such a way that there is little or no overlap and such that little or no restriction of the feeding lumen 122 occurs at the point of attachment between the distal end 121 of the unitary component 117 and the distal end 140 of the catheter 110.

Any of the manners of attachment of the unitary component 117 to the catheter shaft 114 discussed above still avoid the undesirable restriction of the flow associated with the prior art tips having the balloon attached to the interior of the tip (thereby reducing the size of the passageway through the tip which is available for fluid communication). Accordingly, the use of a unitary component 117 (FIGS. 2-8) may enable the user to use a tip 119 (FIGS. 5-8) having a smaller cross-sectional area and/or a smaller sized catheter shaft 114 as the desired level of fluid flow can be achieved in less time under the same use conditions when compared with prior devices having attachments of the balloon to the interior of the tip. It will be appreciated that there are a number advantages or benefits associated with the ability to use a catheter having a smaller shaft diameter where no adverse effects exist as a result of using the catheter with a smaller shaft diameter.

As shown in FIGS. 3-8, the unitary component 117 is designed such that at least a portion of the balloon 118 of the unitary component 117 may be inverted about or around all or a part of the tip 119 of the unitary component 117.

As noted above, as the composition and/or physical characteristics of the catheter 110 and the tip 119 may vary, so too may the composition and/or the physical characteristics of one or more portions or regions of the unitary component 117. That is, for example, the unitary component 117, will have a thickness, however, the thickness, as well as the weight, shape, or density of one or more portions of the unitary component may vary. More specifically, for example, the portion of the unitary component 117 including tip 119 may have different properties (e.g., durometer, thickness, elasticity, density, etc.) from the portion of the component 117 including the balloon 118.

Additionally, within each region or portion of the unitary component 117, the properties and/or characteristics of the component may vary. For example, the tip 119 may be tapered and/or the portion of the unitary component 117 having the balloon 118 may be more expandable or elastic in some areas than in others. It will be appreciated that while the regions or portions of the unitary component 117 are, in some instances herein, referred to separately, they are in fact part of one component, the unitary component 117. It will also be appreciated that while the regions may generally be referred to as separate regions, there is in fact no hard line as to where one region or portion begins and another ends. Thus, what one may refer to as a transition zone, where a part of a portion or region may exhibit the properties and/or characteristics of two regions, may be found in the unitary component 117. A transition zone may even be found within a portion of a unitary component 117. For example, in the portion of a unitary component 117 containing a balloon 118 having different levels of elasticity, there will exist a transition zone between the areas exhibiting different levels of elasticity.

Figure 8:
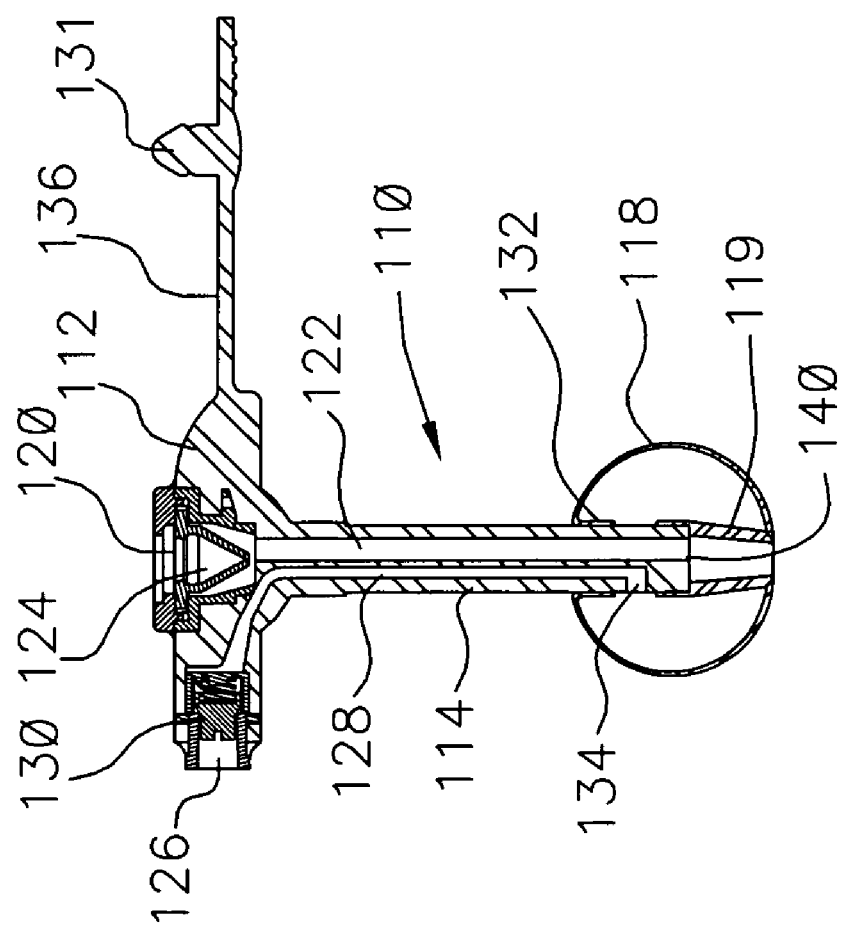
FIG. 8 is a cross-sectional view of the balloon catheter similar to that of FIG. 6, except that the proximal end of the unitary component is invertedly attached to the catheter shaft.

As illustrated in FIGS. 2-4, the unitary component 117 has one end 121 (FIG. 2) adjacent the portion of the unitary component 117 having the tip 119 and a second end 123 adjacent the portion of the unitary component 117 having the balloon 118. The end 123 of balloon 118 which may be inverted about at least part of the tip 119 can be attached to the catheter shaft 114 (FIGS. 3, 3A, 4 and 4A) in a variety of suitable manners. For example, the end 123 may be attached to the exterior of the shaft 114 as shown in FIGS. 3, 3A, 4 and 4A. In those embodiments where the end 123 attaches to the exterior of the catheter 110, the end 123 may be attached so as to form, for example, a cuff 132 (FIGS. 3, 3A, 4 and 4A), or may be attached in an inverted fashion as shown in FIG. 8 and as discussed in commonly assigned co-pending U.S. patent application Ser. No. 10/307,057, entitled "CATHETER HAV- ING A BALLOON MEMBER INVERTEDLY ATTACHED THERETO", filed in the names of Letson et al. on Nov. 30, 2002, the disclosure of which is herein incorporated by reference in its entirety.

It will be appreciated that the size of the catheter 110 as well as the length (inflated and uninflated) of the balloon 118 may be varied in accordance with the size and shape of the body cavity (not shown) the catheter 110 is to be used in and the nature of the matter to be moved through the catheter 110. That is, in some instances, it may be desirable to use catheters 110 having larger and/or wider shafts 114 than in other embodiments. Additionally, as discussed in more detail below the balloon 118 of the catheter 110 may be designed to have a certain size and/or shape in either or both of its inflated or uninflated configurations.

It will also be appreciated that the length of the balloon 118 as well as the point along the shaft 114 at which the end 123 of the balloon 118 is attached may affect the shape of the resulting balloon. Another suitable way of controlling the shape of the resulting inflated balloon 118 includes annular rings such as those shown at 160, 160', and 160" in FIG. 2. Another way of controlling the shape of the inflatable balloon includes, but is not limited to, rotational dipping, commonly done in the condom industry in order to create a uniform film. Still other suitable ways of controlling the shape of the resulting balloon include, but are not limited to, those discussed in the U.S. Pat. No. 6,264,631 B1 to Willis et al., which is incorporated by reference in its entirety.

While the invention has been described in detail with respect to specific embodiments thereof, those skilled in the art, upon obtaining an understanding of the invention, may readily conceive of alterations to, variations of, and equivalents to the described embodiments. It is intended that the present invention include such modifications and variations as come within the scope of the appended claims and their equivalents.

What is claimed is:

1. A catheter comprising:
an elongate shaft, at least a portion thereof having a generally uniform exterior dimension, the shaft including a distal end, a first lumen extending through the shaft and exiting at the distal end, and a second lumen terminating in a port situated upon an exterior lateral surface of the shaft; and
a unitary component comprising a tip and an expandable balloon which are formed continuously from a same piece of material such that no separation of the piece of material exists in the unitary component, the tip configured to have a greater rigidity than the balloon, the tip comprising a generally tubular wall having a passageway formed therethrough and including a proximal end coupled to the distal end of the shaft, wherein the proximal end of the tip is positioned against and abuts the distal end of the shaft without overlap thereon, a distal end comprising an outwardly curved end which curves radially outwardly beyond an outer surface of the tip which is immediately proximal to the outwardly curved end of the tip and away from the passageway thereby creating an enlargement of the diameter of the passageway at the outwardly curved end relative to the diameter of the passageway positioned proximally next to the outwardly curved end, the expandable balloon extending from the outwardly curved end of the tip and, when expanded, extending radially outwardly and away from the outwardly curved end with no overlapping coupling formed between the balloon and the outwardly curved end, wherein no portion of the expandable balloon provides any portion of the wall of the tip defining the passageway, the balloon positioned to overlap and extend proximally over an exterior surface of the tip and a portion of the exterior lateral surface of the shaft, an end of the balloon sealably coupled to the exterior lateral surface of the shaft proximal to the port such that air or fluid provided via the second lumen and through the part inflates the balloon, the passageway of the tip and the first lumen of the shaft cooperating to permit passage of fluid therethrough.

2. The catheter of claim 1 comprising a transition zone at an outermost edge of the curved end and the balloon.

3. The catheter of claim 1 wherein the balloon includes at least one annular ring.

4. The catheter of claim 1 wherein the thickness of one or more portions of the unitary component differ, and wherein the unitary component comprises at least in part an elastomeric material.

* * * * *